US005121741A

United States Patent [19]

Bremer et al.

[11] Patent Number: 5,121,741

[45] Date of Patent: Jun. 16, 1992

[54] SHAPED HALO VEST

[75] Inventors: Paul Bremer; Ross L. Bremer, both of Jacksonville, Fla.

[73] Assignee: Bremer Medical Inc., Jacksonville, Fla.

[21] Appl. No.: 572,004

[22] Filed: Aug. 24, 1990

[51] Int. Cl.[5] .......................... A61H 1/02; A61F 5/02; A61F 5/37

[52] U.S. Cl. ........................................ 602/18; 128/874

[58] Field of Search ...................... 128/874, 75, 78, 69, 128/87 B, 84 R, 84 C, 76 R, DIG. 23

[56] References Cited

U.S. PATENT DOCUMENTS

| | | | |
|---|---|---|---|
| 2,166,229 | 7/1939 | Anderson | 128/84 |
| 2,706,982 | 4/1955 | Hale et al. | 128/87 |
| 3,601,123 | 8/1971 | McFarland | 128/75 |
| 3,605,736 | 9/1971 | D'Amico et al. | 128/75 |
| 3,724,452 | 4/1973 | Nitschke | 128/75 |
| 3,795,243 | 3/1974 | Miller | 128/75 |
| 3,799,156 | 3/1974 | Gurkin | 128/75 |
| 3,827,429 | 8/1974 | Heikes | 128/75 |
| 3,945,376 | 3/1976 | Kuehnegger | 128/78 |
| 4,194,501 | 3/1980 | Watt | 128/75 |
| 4,383,523 | 5/1983 | Schurman | 128/75 |
| 4,502,471 | 3/1985 | Owens | 128/75 |
| 4,515,153 | 5/1985 | Calabrese | 128/75 |
| 4,520,801 | 6/1985 | Lerman | 128/75 |
| 4,539,979 | 9/1985 | Bremer | 128/75 |
| 4,541,421 | 9/1985 | Iverson | 128/87 B |
| 4,620,530 | 11/1986 | Lanier | 128/75 |
| 4,628,913 | 12/1986 | Lerman | 128/78 |
| 4,632,099 | 12/1986 | Mollo | 128/87 |
| 4,665,564 | 5/1987 | Bogart | 2/119 |
| 4,677,969 | 7/1987 | Calabrese | 128/75 |
| 4,732,144 | 3/1988 | Cunanan | 128/878 |
| 4,807,605 | 2/1989 | Mattingly | 128/75 |
| 4,913,135 | 4/1990 | Mattingly | 128/78 |

*Primary Examiner*—Robert A. Hafer
*Assistant Examiner*—Michael Brown
*Attorney, Agent, or Firm*—Nixon & Vanderhye

[57] ABSTRACT

A shaped halo vest includes front and back vest components for overlying the front and back of the patient's upper torso. Each component is shaped three-dimensionally to load selected areas of the body, i.e., selected muscle groups, and avoid loading other selected areas of the body, i.e., bony prominences. The shaping includes three-dimensional compound curves for bowing the molded plastic vest components inwardly to transfer loads or outwardly to avoid transfer of loads. The marginal edges of the vest components are flared outwardly to avoid pinching or bruising the underlying tissue upon relative movement of the patient and vest. The three-dimensional compound curves and the flared edges contribute to the structural rigidity of the vest. The front and back components are secured one to the other by adjustable straps along the opposite sides of the lower portions of the vest and adjustable length shoulder straps. Vent holes are provided in the back vest component.

24 Claims, 5 Drawing Sheets

SHAPED HALO VEST

BACKGROUND AND SUMMARY OF THE INVENTION

The present invention relates to halo vests for use by patients with cervical or spinal injuries for immobilizing the neck of the patient to promote healing and particularly relates to a halo vest that is molded or shaped three-dimensionally to load specific muscle groups of the patient's body and avoid loading of other body portions, such as bony prominences.

Halo vests are orthopedic devices normally applied by a medical practitioner, such as an orthopedic or neurological surgeon, to a patient having cervical or spinal injuries for immobilizing the patients to promote healing which often takes many months. Conventional halo vests typically comprise a vest body having front and rear components for overlying the front and back of the patient's upper torso. The front and back body components are normally secured one to the other by flexible straps around the waist and over the shoulders. Halo support rods attach to and upstand from upper portions of the front and back body components for supporting a halo about the patient's head, the head being secured within the halo by a surgical procedure. A typical halo vest is described and illustrated in co-pending U.S. patent application Ser. No. 07/474,288, filed Feb. 5, 1990, that particular application being directed to an improved lining for the front and back components of the vest body.

The front and back components of a typical halo vest are often formed of flat pieces of material, trimmed to the desired shape or outline and then bent or curved into a shape to encompass the upper torso. The bending is essentially a two-dimensional, non-compound bend so that the front and back components will substantially parallel the lateral curvature of the upper torso. Trimming the components to a particular outline avoids some of the problems associated with supporting the vest on certain parts of the body, such as bony body prominences. However, certain bony prominences cannot be avoided by trimming or outlining. Thus, conventional halo vests typically rest on and are supported by, albeit with padding disposed therebetween, certain of the bony prominences of the body. This not only can lead to patient discomfort but the pressure or load of the halo vest on the bony prominences tends to destroy the skin and tissue between the prominences and the material of the vest components. Ulceration of the skin frequently occurs. These problems have long been recognized. However, the typically preferred solutions to these problems, for example, to avoid the bony prominences in the spinal area on the back of the patient, have been to apply more padding or attempt to trim the vest components about them. Trimming, of course, is severely limited because of the distribution of the bony prominences about the body and the need for structural support for the halo from a relatively rigid structural vest which, in turn, transmits the loading to the patient's body. Additional padding is not a solution because, even with padding, there is a compacted mass of material between the hard vest component and the bony prominence which prevents moisture from escaping between the skin and the vest and hence promotes skin and tissue problems.

Additionally, many conventional vests, when trimmed, are left with flat or relatively sharp edges. Upon patient movement, the sharp edges oftentimes pinch the adjoining skin. This can cause substantial annoying irritation and bruising of the skin and, of course, patient discomfort.

According to the present invention, there is provided a shaped halo vest having front and back components which are not only trimmed to the desired outline, but are shaped or molded three-dimensionally to (a) transfer loads imposed by the vest to the patient's body only onto specific and selected muscle groups; (b) avoid transfer of loads from the vest onto other selected areas of the body, i.e., bony prominences; and (c) avoid sharp pressure points on the patient's skin along their marginal edge. Additionally, the molded or shaped three-dimensional compound curves of the front and back components of the present halo vest enhance the strength and structural rigidity of the vest whereby such shape enables the vest to be formed of reduced material and weight. By selective three-dimensional shaping of the vest components, loading on the vest can be transferred to selected locations along the upper torso to avoid bony prominences, to load selected muscle groups which can withstand the loading, and also to increase air circulation between the vest and the patient's body. The present vest is therefore skin tissue-friendly and avoids many of the problems associated with the continuous application of pressure and loading onto various areas of the body.

As an example of the shaping of the vest components according to the present invention, it will be appreciated that the vest back component overlies the spinous processes. These constitute bony prominences along the spine. In that area, the vest back is three-dimensionally shaped to avoid application of pressure to those prominences. Accordingly, the back component is bowed outwardly as well as curved in a vertical direction in the area thereof that overlies and registers with the spinous processes. The lining follows this compound curvature of the vest back component and, hence, produces a spacing between the vest and the patient's body, enabling flow of air therebetween. More particularly, openings are provided through the back vest component in areas overlying the spinous processes. The openings lie in the outwardly directed bulbous parts and hence enable air to circulate between the vest liner and the patient's skin.

Concomitantly, the back vest component is shaped to transfer loadings on the vest to selected muscle groups for supporting the vest. For example, the back vest component is shaped, i.e., bowed inwardly three-dimensionally, in selected areas therealong to distribute the loadings on the vest to the trapezius, latissimus dorsi and erector spinae muscle groups on opposite sides of the spinous processes and laterally inwardly of the spine of the scapula and the tendons connecting it and the trapezius muscle. Thus, the back vest component is shaped to apply loadings along these muscle groups in generally vertical extended areas on either side of the spinous processes from the neck down to the bottom of the rib cage. Loading is therefore applied to the desired areas of the body and not applied to those areas which are likely to cause damage to the underlying skin and tissue or cause patient discomfort.

The front vest component is similarly shaped to avoid application of loadings to selected areas and to apply loadings to other selected areas. Thus, the front vest component is three-dimensionally bowed outwardly along a central vertically extending portion overlying the sternum while laterally outwardly and on opposite sides of the central portion the front vest component is bowed three-dimensionally inwardly to apply loadings to the underlying pectoralis muscle groups.

In accordance with a further aspect of the present invention, the marginal edges of the front and back vest components are flared outwardly. Any relative movement between the vest and the individual's body thus avoids application of sharp pressure points along the patient's skin adjacent the outline of the vest components. The three-dimensional shaping on the front and back vest components including the flared margins also increases the structural strength of the vest components, enabling use of thinner materials as compared with the thickness of the materials used in conventional vests and hence a lighter vest.

There are various other improvements in the present vest which will become apparent upon reference to the specifically disclosed embodiment of the vest. Such improvements include shoulder straps dimensioned to overlie an area of the shoulder between the bony prominences and the patient's neck, hence, increasing the comfort of the patient and avoiding problems associated with loadings on the patient's skin. Additionally, the straps about the sides of the torso joining the lower ends of the front and back vest components are of unique configuration, as will be pointed out in the ensuing description.

In a preferred embodiment according to the present invention, there is provided a halo vest for a human wearer, comprising a vest body of structural material having front and back components for overlying the front and back, respectively, of the wearer. Halo support elements are secured to the vest body. The vest body has first discrete portions for transferring loading on the vest including from the halo support elements to first selected areas of the wearer's body underlying and registering with the first discrete portions, respectively, and second discrete portions, spaced from the first discrete portions, for avoiding transfer of loading on the vest, including from the halo support elements, to second selected areas of the wearer's body underlying and registering with the second discrete portions, respectively.

In a further preferred embodiment according to the present invention, there is provided a vest for a human wearer, comprising a vest body of substantially rigid molded structural plastics material having front and back components for overlying the front and back, respectively, of a wearer. Support elements are provided on the body for supporting loads. The vest body has first discrete portions for transferring loading from the support elements to first selected areas of the wearer's body underlying and registering with the first discrete portions, respectively, and second discrete portions spaced from the first discrete portions, for avoiding transfer of loading on the vest, including from the support elements to second selected areas of the wearer's body underlying and registering with the second discrete portions, respectively, the second discrete portions including portions on the back component for bridging the spinal processes and portions of the front component for bridging the sternum, the first portions located along the back component for overlying the trapezius, latissimus dorsi and erector spinae muscle groups and the first portions located along the front component for overlying the pectoralis muscle groups, the bridging portions comprising three-dimensional outwardly curved molded portions.

Accordingly, it is a primary object of the present invention to provide a novel and improved halo vest which is shaped three-dimensionally in selected areas of its front and back components to transfer loadings on the vest to selected areas of the body and avoid transfer of loadings on the vest to other selected areas of the body, i.e., bony prominences, whereby a vest of increased comfort, structural rigidity and increased friendliness to skin tissue is provided.

These and further objects and advantages of the present invention will become more apparent upon reference to the following specification, appended claims and drawings.

BRIEF DESCRIPTION OF THE DRAWING FIGURES

Figure 4:
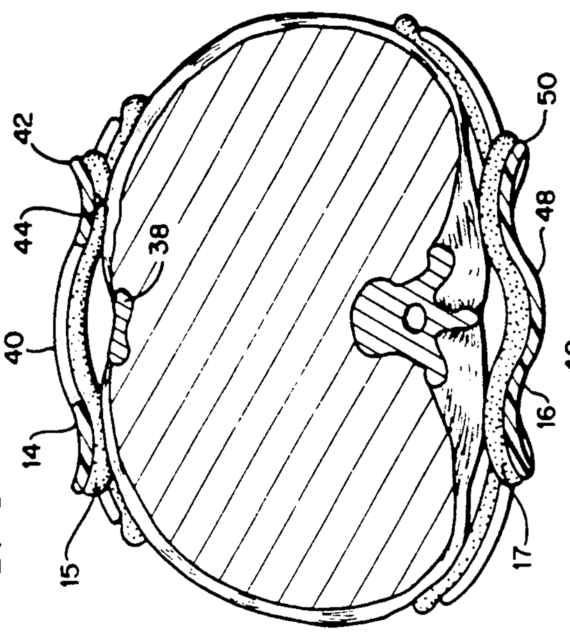
Figure 5:
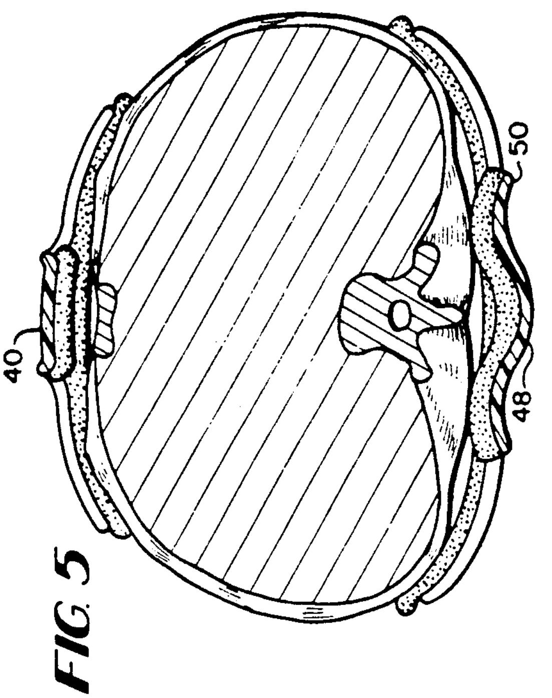
Figure 2:
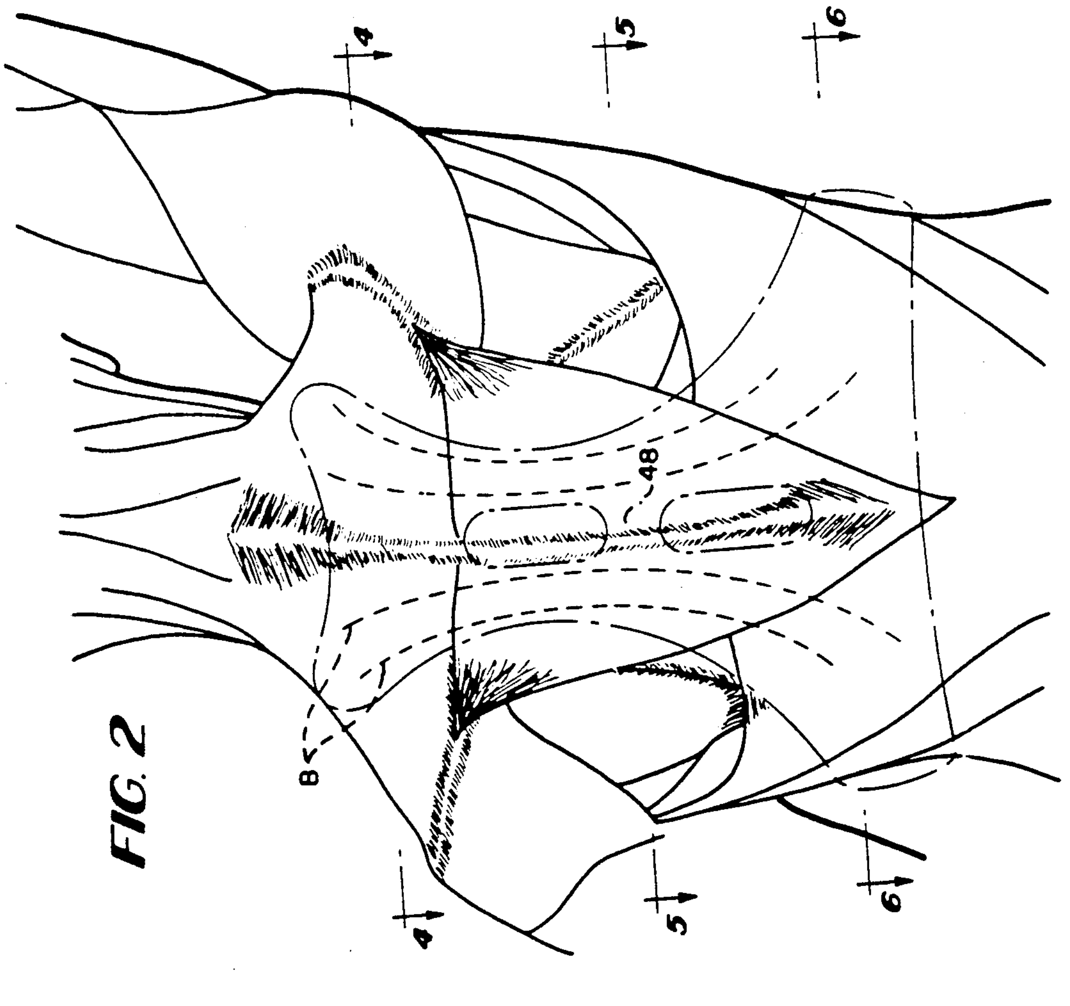
FIG. 2 is a fragmentary illustration of certain bony prominences and muscle groups in the back of a patient with the back vest component shown in dashed lines overlying the patient's back.
Figure 6:
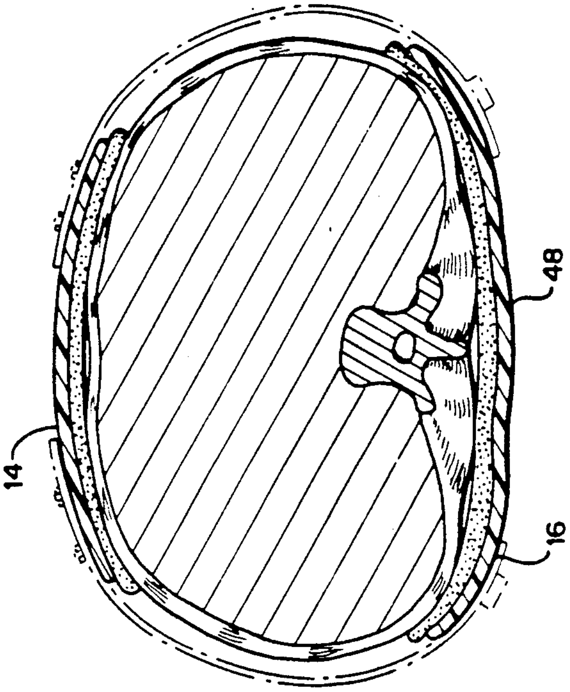
Figure 3:
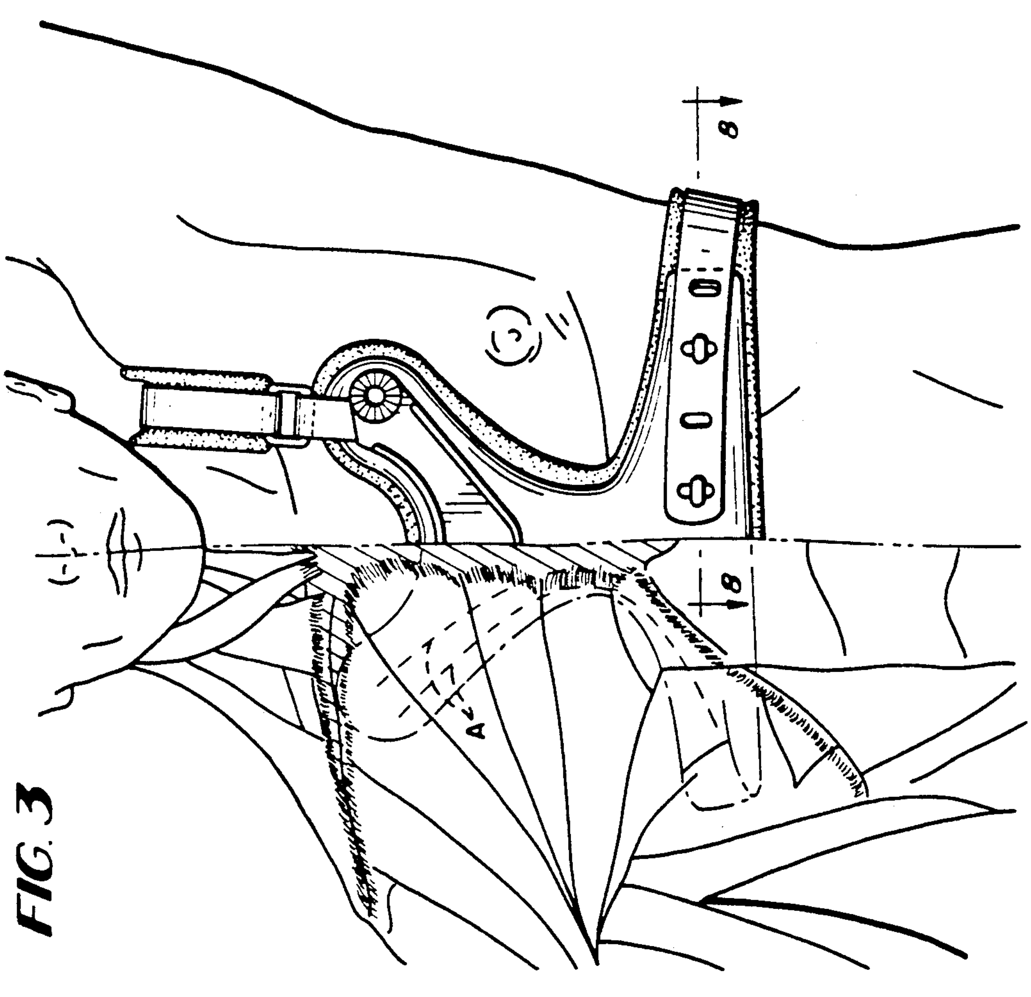
FIG. 3 is a view similar to FIG. 2 illustrating certain muscle groups and bony prominences along the upper front torso of a patient and portions of the front vest component shown in dashed and full-line configurations overlying the patient's upper front torso.
Figure 9:
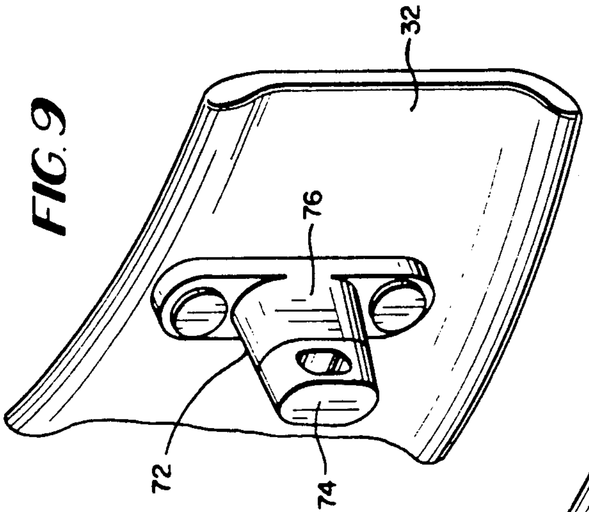
Figure 10:
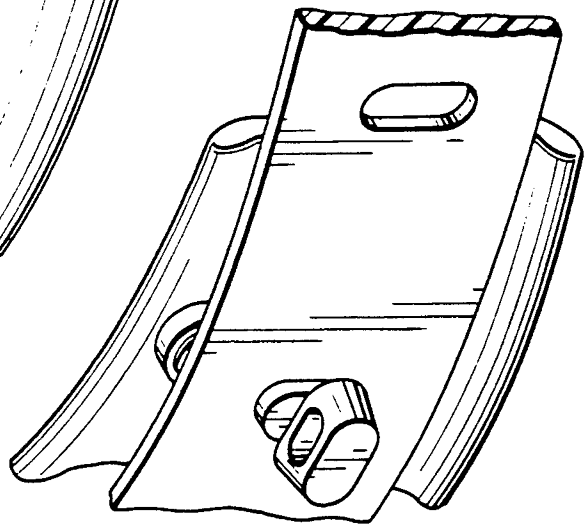
Figure 7:
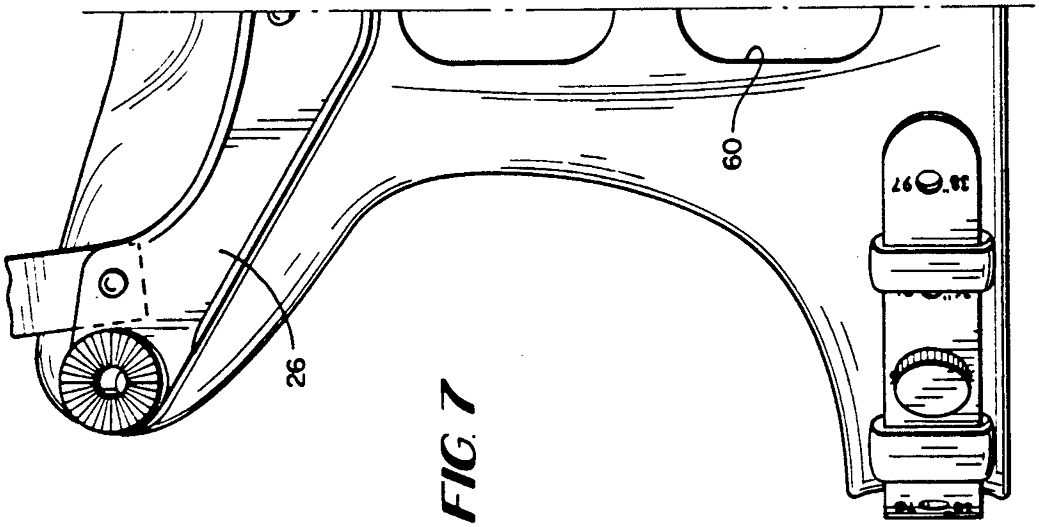
Figure 11:
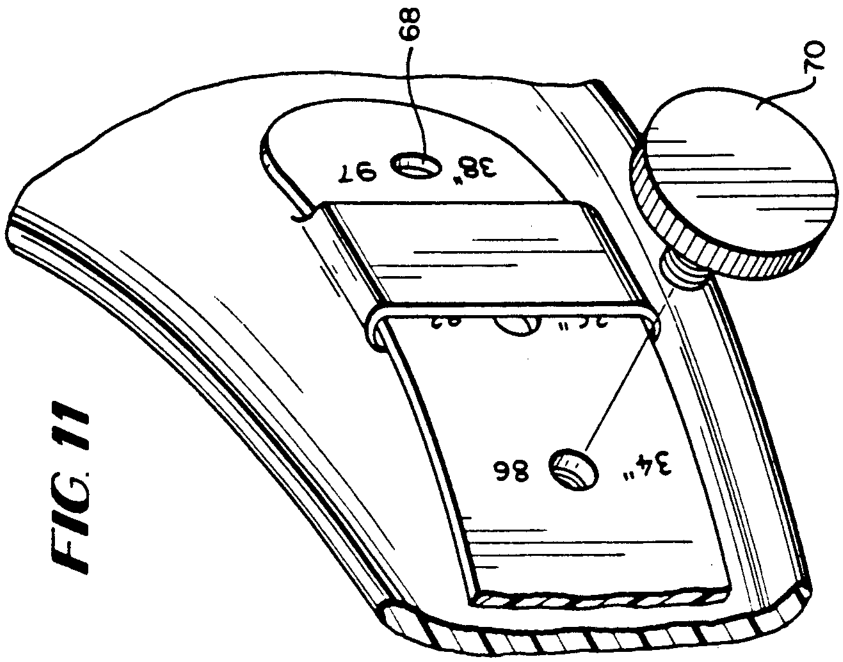
Figure 8:
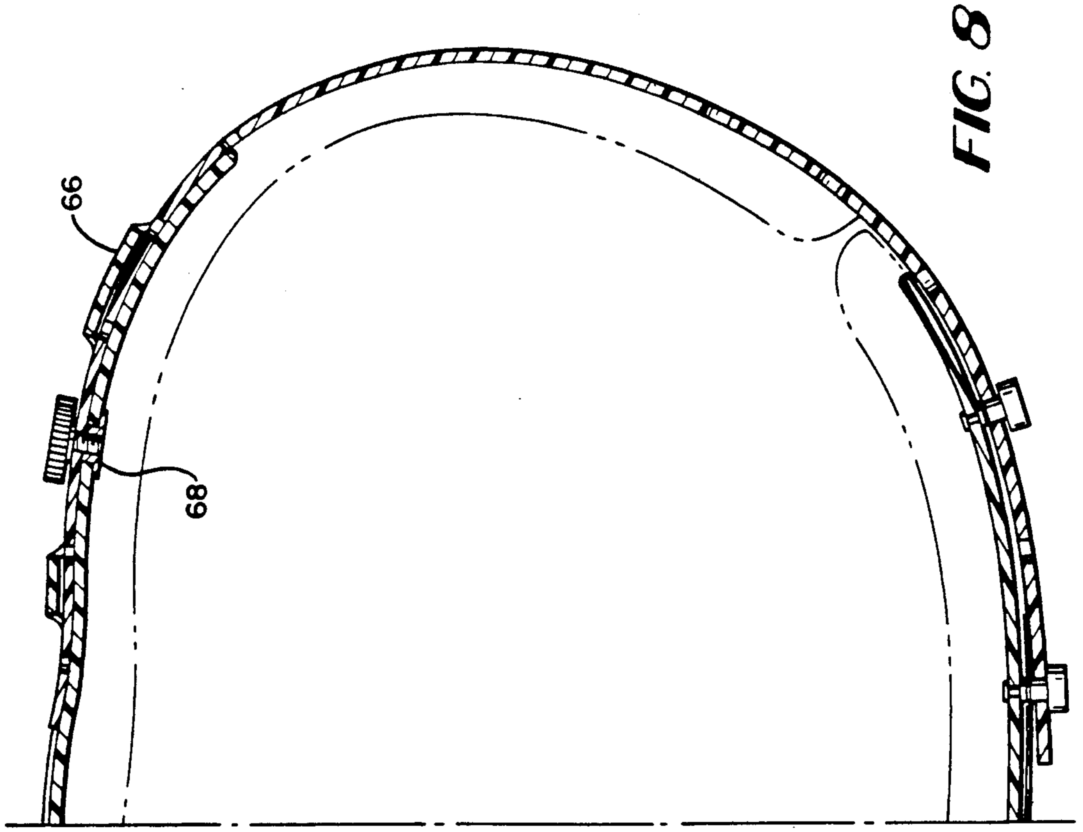

FIG. 4, 5 and 6 are cross-sectional views taken generally about on lines 4—4, 5—5 and 6—6, respectively, in FIG. 2;

FIG. 7 is an enlarged partial front elevational view of the front component of the halo vest illustrating the side connections;

FIG. 8 is an enlarged cross-sectional view taken generally about on lines 8—8 in FIG. 3;

FIG. 9 is an enlarged fragmentary view of a fastener formed on the strap connecting the front and back components of the vest;

FIG. 10 is a view similar to FIG. 9 illustrating the overlying strap and the connection with the underlying strap; and FIG. 11 is an enlarged fragmentary perspective view illustrating the side strap connection adjacent the back component of the vest.

DETAILED DESCRIPTION OF THE DRAWING FIGURES

Reference will now be made in detail to a present preferred embodiment of the invention, an example of which is illustrated in the accompanying drawings.

Figure 1:
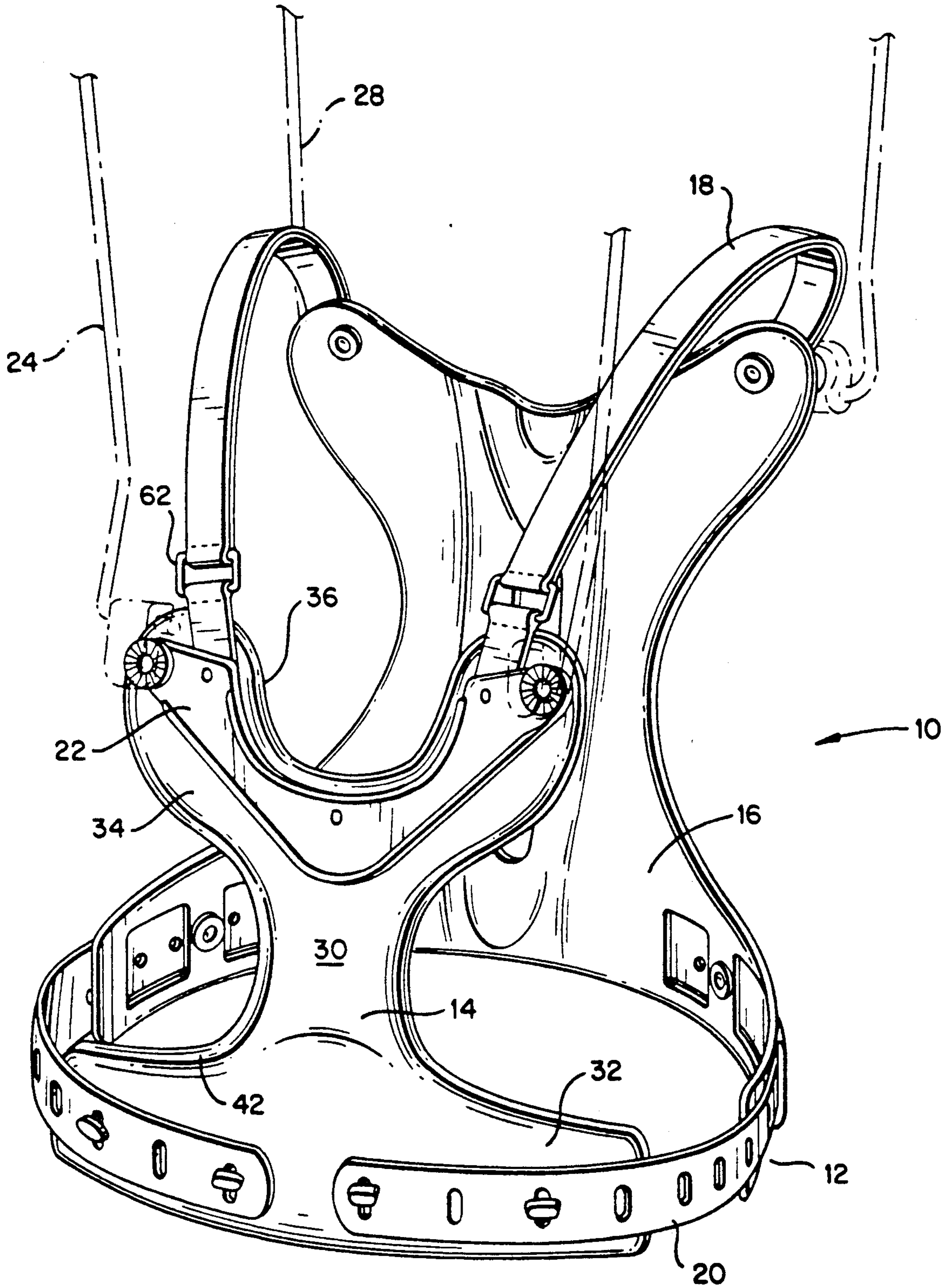
FIG. 1 is a perspective view of a shaped halo vest constructed in accordance with the present invention illustrating the front component of the vest in the foreground.

Referring now to FIG. 1, there is illustrated an example of a halo vest, generally designated 10, constructed in accordance with the present invention and including a vest body 12 having front and back components 14 and 16, respectively. The front and back vest components are lined along their interior faces, as indicated at 15 and 17, respectively, and such lining may comprise the lining described and illustrated in co-pending application Ser. No. 07/474,288, filed Feb. 5, 1990, the disclosure of which is incorporated herein by reference. Adjustable-length flexible shoulder straps 18 connect the upper ends of the vest components 14 and 16 one to the other, while substantially rigid plastic straps 20 connect the lower portions of the front and back vest components 14 and 16 one to the other. These components are similarly lined with fleece material. A support plate 22 overlies and is secured to an upper part of the front vest component 14, affording a mounting for the front upstanding halo support rods illustrated in dashed line at 24. A similar structural support plate 26 is secured along the upper part of back component 16 (FIG. 7) and similarly secures upstanding halo support rods 28 to the vest. The upper ends of the support rods 24 and 28 connect with cross-braces for connection to a halo, not shown. The support rods 24, 28, the halo, not shown, the cross-braces, and the support structures 22 and 26 are conventional constructions and form no part of the present invention.

In accordance with the present invention, the front and back vest components 14 and 16 are each trimmed to a predetermined outline, essentially modified hourglass configurations, and are three-dimensionally shaped such that (a) loadings from the vest are applied to selected areas of the patient's body; (b) loadings from the vest are not transferred to other selected areas of the patient's body, i.e., bony prominences and the like; and (c) the edges of the front and back vest components 14 and 16 flare outwardly to avoid pinching or otherwise sharply engaging with the patient's skin upon relative movement between the vest and the patient's body. The flared edges and the compound curves in the front and back vest components in and along selected areas thereof additionally afford structural rigidity to the vest.

To provide the compound three-dimensional curve, the vest components 14 and 16 are preferably molded of plastic material. For example, the components may be molded of a high-density polyethylene material.

Referring now particularly to FIG. 1, the general hourglass configuration of front vest component 14 is provided by a central portion 30, a pair of lower, rearwardly extending, lateral portions 32 and upwardly and laterally extending upper portions 34 defining a deep arcuate groove 36 therebetween. It will be appreciated from a review of FIGS. 4, 5 and 6, that the front component 14 is shaped generally in an inwardly bowed or concave configuration to generally conform to the lateral shape of the upper front torso. Also, the front component 14 is curved inwardly, i.e., bowed to a shallow concave shape, in a vertical direction through the central portion 30, again generally conforming to the curvature of the upper front torso of the patient in the vertical direction.

In addition, and in accordance with the present invention, the front vest component 14 has compound curvatures in various areas constituting first and second discrete portions thereof to respectively load or avoid loading the patient's body in selected areas. Thus, where the front portion 14 overlies the sternum, designated 38 in FIGS. 4 and 5, the upper central portion between portions 34 and the central portion 30 is bowed outwardly at 40, thus spacing the front vest component 14 from the skin overlying the sternum. Accordingly, in the area of the bony prominences of the sternum, particularly adjacent the upper end of the sternum, the front component 14 is shaped, e.g., bowed outwardly to avoid application of any pressure or loading on those bony structures.

Importantly, the molded shape of the front component 14, particularly in those areas 44 of the front vest component between its edges and the outwardly bowed central portion 40, enables those areas 44 to have a generally inwardly bowed shape for transferring loads onto the selected and predetermined portions of the individual's torso for supporting the loadings on the vest. Thus, the areas 44 load to the pectoralis muscle groups on opposite sides of the sternum. It will therefore be appreciated that the areas 44 extend outwardly and upwardly in the upper portions 34, as well as laterally in the lateral portions 32, to bear on selected muscle areas generally as illustrated by the dashed lines A in FIG. 3. Thus, the front vest component applies loading to the patient's body along opposite sides of the sternum on the pectoralis muscle groups and inwardly of the margins of the front vest component because of the flared edges thereof.

Additionally, as can be seen from a review of FIGS. 4, 5 and 9, the marginal edges of the front component 14 are flared outwardly, for example, at 42, substantially along the entire outline or edge of component 14, with the exception of the ends of the lateral portions 32. This avoids pinching the patient's skin during relative movement of the patient's body and the vest and structurally reinforces the front vest component.

Referring to FIGS. 1 and 4–6, the back vest component 16 is similarly shaped and molded to provide compound curves whereby the vest is specifically configured to transfer loading onto selected portions of the body and to avoid transference of loading onto other selected portions of the body. For example, it will be appreciated from a review of FIGS. 4, 5 and 6 that the back component 16 is generally concave along its inner surface to substantially conform to the lateral configuration of the patient's back. The back component 16 is also generally concave in a vertical direction along a vertical centerline thereof to substantially conform to the vertical curved configuration of the patient's back. Consequently, back component 16, similarly as front component 14, has an initial generally compound curvature in both vertical and horizontal directions.

In addition to that curvature, and in accordance with the present invention, back component 16 is further shaped three-dimensionally to transfer loadings onto selected areas, i.e., selected muscle groups, and to avoid transference of loadings onto other areas of the torso, i.e., bony prominences. To accomplish this, the central vertically extending portion 48 of back component 16 is bowed outwardly to thus increase the spacing between the back vest component 16 and the spinal column area and the bony prominences thereof. This outwardly bowed portion extends substantially the full height of the back component 16. Similarly as the front component, the marginal edges of the back component are flared outwardly at 50, with the exception of the ends of the lower lateral portions. Thus, the areas between the outwardly bowed concave portion 48 and the flared edges 50 provides an inwardly bowed convex surface which extends along the back of the patient for bearing and transferring loading from the vest onto the elected areas of the body, i.e., the trapezius, latissimus dorsi and erector spinae muscle groups. Thus, areas designated by the dashed lines B in FIG. 2 overlying the trapezius muscle group between the spinous processes and the spine of the scapula and associated tendons, as well as the latissimus dorsi, bear the loading of the back vest component. Back component 16 is also provided with a pair of vertically spaced, substantially oval-shaped openings 60, which provide for ingress of air through similarly shaped openings in the liner. The central portion 48 defining the ends of these openings 60 are bowed outwardly and hence the openings therethrough and registering openings through the liner are spaced outwardly of the patient's spinous processes and from the skin to provide an air gap therebetween.

It will be seen that the compound nature of the curves provided in the surface of the front and back components 14 and 16, respectively, afford additional structural rigidity to the vest, while at the same time selectively load or not load selected areas of the patient's body.

It will therefore be appreciated that the front and back vest components have first and second discrete portions, respectively, for transferring loads to and avoiding load transfer to registering and underlying areas of the patient's body. The outwardly and inwardly bowed areas of the vest components thus space the vest in those areas from the patient's body to a greater or lesser extent, respectively. Also, the vest components each have generally sinuous or W-shaped cross-sections both vertically and horizontally. The generally sinuous horizontal cross-section is illustrated, for example, in FIGS. 4 and 5. Vertically, the flared edges in combination with the concave nature of the components in that direction afford a generally sinuous cross-section.

Shoulder straps 18 extend from ends fixed between the support structure 26 and the back component 16 forwardly for looping through buckles 62 formed on strips secured between the front support structure 22 and front component 14. Straps 18 are therefore adjustable in length and are preferably provided with hook-and-loop material, such as Velcro, to facilitate adjustment of the length of the straps. The straps are somewhat narrow, approximately 1 inch in width, and are provided with underlying shoulder pad portions, not shown, formed of linear material.

To connect lower portions of the front and back components 14 and 16 together, lower straps 20 each comprise an individual flexible strap formed of plastic material affording some structural rigidity to the straps. Along the lateral portions of back component 16, there are provided pairs of integrally molded outwardly projecting loops 66 for receiving one end of straps 20. The straps are provided with a plurality of openings 68, preferably equally spaced one from the other. A portion of the back component between loops 66 is provided with a hole and a female-threaded washer 68 along the inside face of the strap. A securing knob 70 having a male thread extends through the selectively aligned openings 68 of the strap and the opening in the back component 16 securing the strap to the latter by threading knob 70 into the washer 68.

Along the front side of each strap 20, there is provided a plurality of equally spaced openings, generally oval in shape, for overlying a pair of fasteners 72, which project from each lateral portion 32 of the front component 14. Fasteners 72 have generally complementary oval-shaped projections, the outer ends of which projections 74 are rotatable relative to the base projections 76. Thus, upon insertion of a pair of the oval-shaped openings about fasteners 72, outer projections 74 may be rotated into a locking position, as illustrated in FIG. 10. Thus, by selectively adjusting the position of the straps both on the front and back components 14 and 16, respectively, the tightness or looseness of the vest may be readily adjusted.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A halo vest for a human wearer, comprising:

a vest body of structural material having front and back components for overlying the front and back, respectively, of the wearer; and halo support elements secured to said vest body, said vest body having first discrete portions for transferring loading on the vest including from said halo support elements to first selected areas of the wearer's body underlying and registering with said first discrete portions, respectively, and second discrete portions, spaced from said first discrete portions, for avoiding transfer of loading on the vest, including from said halo support elements, to second selected areas of the wearer's body underlying and registering with said second discrete portions, respectively, one of said first and second discrete portions comprising three dimensional portions of said body curved in both vertical and horizontal directions.

2. A vest according to claim 1 wherein said one of said first and second discrete portions comprises said first discrete portion, said three-dimensional portions of said first discrete portion comprising compound curves bowed inwardly toward the wearer s body for applying loading thereto.

3. A vest according to claim 1 wherein said one of said first and second discrete portions comprises said second discrete portion, said three-dimensional portions of said second discrete portion comprising compound curved portions bowed outwardly from the wearer's body.

4. A vest according to claim 1 wherein said first and second discrete portions comprise three-dimensional compound portions curved in both vertical and horizontal directions and bowed inwardly and outwardly, respectively, for spacing said second discrete portions a distance from the second selected areas of the wearer's body greater than the distance said first discrete portions are spaced from the first selected areas of the wearer's body.

5. A vest according to claim 1 wherein said back vest component has exterior and interior surfaces and a second discrete portion extending generally longitudinally along substantially a vertical centerline of said back component for overlying the spinous processes, said second discrete portion of said back vest component having a lateral extent sufficient to laterally span the spinous processes.

6. A vest according to claim 5 including a lining along the interior surface of said back vest component and shaped similarly as said second discrete portion overlying the spinous processes to define an air flow channel between said liner and the spinal processes.

7. A vest according to claim 6 including openings through said back component and said lining for admitting air through the vest.

8. A vest according to claim 1 wherein said vest body has edges defining the outline thereof, said edges being flared outwardly to form generally convex interior surfaces in opposition to underlying registering portions of the wearer's body.

9. A vest according to claim 1 wherein said vest body is formed of a molded plastic material.

10. A vest according to claim 1 wherein said first and second discrete portions comprise three-dimensional compound portions curved in both vertical and horizontal directions and bowed inwardly and outwardly, respectively, for spacing said second discrete portions a distance from the second selected areas of the wearer's body greater than the distance said first portions are spaced from the first selected areas of the wearer's body, said vest body having edges defining the outline thereof, said edges being flared outwardly to form generally convex interior surfaces in opposition to underlying registering portions of the wearer's body, at least one of said front vest component and back vest component having, in vertical or horizontal cross-section, a sinuous configuration.

11. A vest according to claim 1 wherein at least one of said front vest component and said back vest component has in one of vertical or horizontal cross-section, a sinuous configuration.

12. A vest according to claim 1 wherein each of said front vest component and said back vest component has, in at least one vertical or horizontal cross-section, a sinuous configuration.

13. A vest according to claim 1 wherein each of said front vest component and said back vest component has, in both vertical and horizontal cross-sections, a sinuous configuration.

14. A vest according to claim 1 including straps for laterally interconnecting lower portions of said front and back components and cooperable means on each of said front and back components and said straps for adjusting the length of said straps at each of the connections thereof with the front and back vest components.

15. A vest for a human wearer, comprising:

a vest body of substantially rigid molded structural plastics material having front and back components for overlying the front and back, respectively, of a wearer;

support elements on said body for supporting loads;

said vest body having first discrete portions for transferring loading from said support elements to first selected areas of the wearer's body underlying and registering with said first discrete portions, respectively, and second discrete portions spaced from said first discrete portions, for avoiding transfer of loading on the vest, including from said support elements to second selected areas of the wearer's body underlying and registering with said second discrete portions, respectively, said second discrete portions including portions on said back component for bridging the spinal processes and portions of said front component for bridging the sternum, said first portions located along said back component for overlying the trapezius, latissimus dorsi and erector spinae muscle groups and said first portions located along said front component for overlying the pectoralis muscle groups;

said bridging portions comprising three-dimensional outwardly curved molded portions.

16. A vest according to claim 15 wherein said first discrete portions comprise compound curves bowed inwardly toward the wearer's body for applying loading thereto.

17. A vest according to claim 15 wherein said first and second discrete portions comprise compound curved portions bowed inwardly and outwardly, respectively, for spacing said second vest body portion a distance from the second selected areas of the wearer's body greater than the distance said first vest body portion is spaced from the first selected areas of the wearer's body.

18. A vest according to claim 15 wherein said vest body has edges defining the outline thereof, said edges being flared outwardly to form generally convex interior surfaces in opposition to underlying registering portions of the wearer's body.

19. A vest according to claim 18 wherein said vest body is formed of a molded plastic material.

20. A vest according to claim 15 wherein said first and second discrete portions comprise compound curved portions bowed inwardly and outwardly, respectively, for spacing said second vest body portion a distance from the second selected areas of the wearer's body greater than the distance said first vest portion is spaced from the first selected areas of the wearer's body, said vest body having edges defining the outline thereof, said edges being flared outwardly to form generally convex interior surfaces in opposition to underlying registering portions of the wearer's body, at least one of said front vest component and back vest component having, in vertical or horizontal cross-section, a sinuous configuration.

21. A vest according to claim 15 wherein at least one of said front vest component and said back vest component has in one of vertical or horizontal cross-section, a sinuous configuration.

22. A vest according to claim 15 wherein each of said front vest component and said back vest component has, in at least one vertical or horizontal cross-section, a sinuous configuration.

23. A vest according to claim 15 wherein each of said front vest component and said back vest component has, in both vertical and horizontal cross-sections, a sinuous configuration.

24. A vest according to claim 15 including straps for laterally interconnecting lower portions of said front and back components and cooperable means on each of said front and back components and said straps for adjusting the length of said straps at each of the connections thereof with the front and back vest components.

* * * * *